US009440234B2

(12) United States Patent
Nordberg et al.

(10) Patent No.: US 9,440,234 B2
(45) Date of Patent: Sep. 13, 2016

(54) DEVICE FOR ANALYSIS OF A TARGET ANALYTE

(71) Applicant: RareCyte, Inc., Seattle, WA (US)

(72) Inventors: Joshua Nordberg, Bainbridge Island, WA (US); Jennifer Chow, Seattle, WA (US); Daniel Campton, Seattle, WA (US); Jonathan Lundt, Missoula, MT (US)

(73) Assignee: RareCyte, Inc., Seattle, WA (US)

( * ) Notice: Subject to any disclaimer, the term of this patent is extended or adjusted under 35 U.S.C. 154(b) by 292 days.

(21) Appl. No.: 14/220,670

(22) Filed: Mar. 20, 2014

(65) Prior Publication Data

US 2014/0287486 A1 Sep. 25, 2014

Related U.S. Application Data

(60) Provisional application No. 61/804,280, filed on Mar. 22, 2013.

(51) Int. Cl.
*B01L 3/00* (2006.01)
*C12Q 1/68* (2006.01)

(52) U.S. Cl.
CPC ........ *B01L 3/50855* (2013.01); *B01L 3/50851* (2013.01); *B01L 2300/0822* (2013.01)

(58) Field of Classification Search
CPC .................. B01L 2300/0822; B01L 3/50851; B01L 3/50855
See application file for complete search history.

(56) References Cited

U.S. PATENT DOCUMENTS 6,096,562 A * 8/2000 Bunn et al. ........... B01L 3/5021 422/509
8,034,306 B1 * 10/2011 Grudzien et al. ... B01L 3/50853 422/552
2008/0288178 A1 * 11/2008 Frazier ............ G01N 27/44721 702/20
2010/0112683 A2 * 5/2010 Atwood .............. B01L 3/50851 435/303.1
2010/0173394 A1 * 7/2010 Colston, Jr. ........... B01F 3/0807 435/287.2
2011/0212453 A1 * 9/2011 Agarwal .......... G01N 35/00029 435/6.12
2012/0052560 A1 3/2012 Knight et al.
2012/0135511 A1 5/2012 Battrell et al.
2012/0171678 A1 7/2012 Maltezos et al.

FOREIGN PATENT DOCUMENTS

KR 20120138747 A 12/2012

* cited by examiner

*Primary Examiner* — Gautam Prakash

(57) ABSTRACT

This disclosure is directed to a slide for analyzing target analytes of a suspension. The slide can be used to collect and hold the target analyte for imaging or further processing. The slide comprises a well section, including wells into which the target analyte can be stored. The wells may be removable and sized to fit into a second apparatus, such as a PCR thermocycler, for additional processing. Alternatively, the wells may hold processing vessels, such as PCR tubes, the processing vessels being used for downstream processing and/or analysis.

16 Claims, 8 Drawing Sheets

DEVICE FOR ANALYSIS OF A TARGET ANALYTE

CROSS-REFERENCE TO A RELATED APPLICATION

This application claims the benefit of Provisional Application No. 61/804,280, filed Mar. 22, 2013.

TECHNICAL FIELD

This disclosure relates generally to a device for analysis of a target analyte, though more specifically, to a slide for isolating and/or processing the target analyte.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as fetal cells, endothelial cells, epithelial cells, parasites, bacteria, and inflammatory cells, and viruses, including HIV, cytomegalovirus, hepatitis C virus, and Epstein-Barr virus and nucleic acids. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 3 CTCs is considered clinically relevant in the diagnosis and treatment of a cancer patient. However, detecting even 1 CTC in a 7.5 ml blood sample may be clinically relevant and is equivalent to detecting 1 CTC in a background of about 50 billion red and white blood cells. Using existing techniques to find, isolate and extract as few as 3 CTCs of a whole blood sample is extremely time consuming, costly and is extremely difficult to accomplish.

As a result, practitioners, researchers, and those working with suspensions continue to seek systems and methods to more efficiently and accurately detect, isolate and extract target materials of a suspension.

DETAILED DESCRIPTION

This disclosure is directed to a slide for analyzing target analytes of a suspension. The slide can be used to collect and hold the target analyte for imaging or further processing. The slide comprises a well section, including wells into which the target analyte can be stored. The wells may be removable and sized to fit into a second apparatus, such as a PCR thermocycler, for additional processing. Alternatively, the wells may hold processing vessels, such as PCR tubes, the processing vessels being used for downstream processing and/or analysis.

Figure 1A:
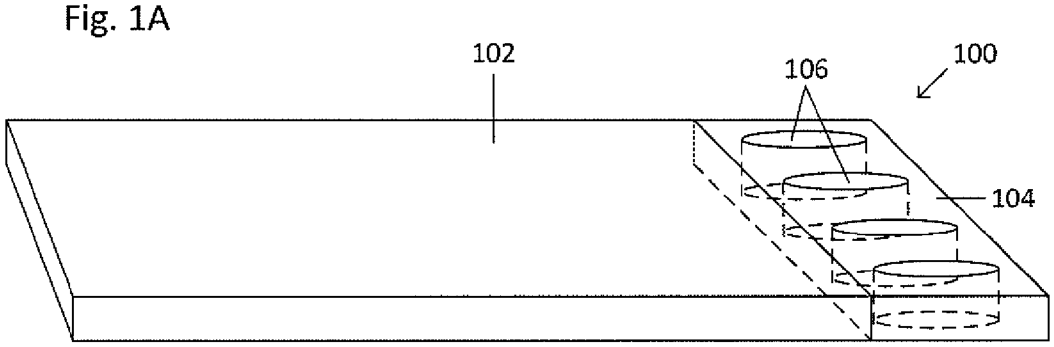
FIGS. 1A-1B show an example slide.
Figure 1B:
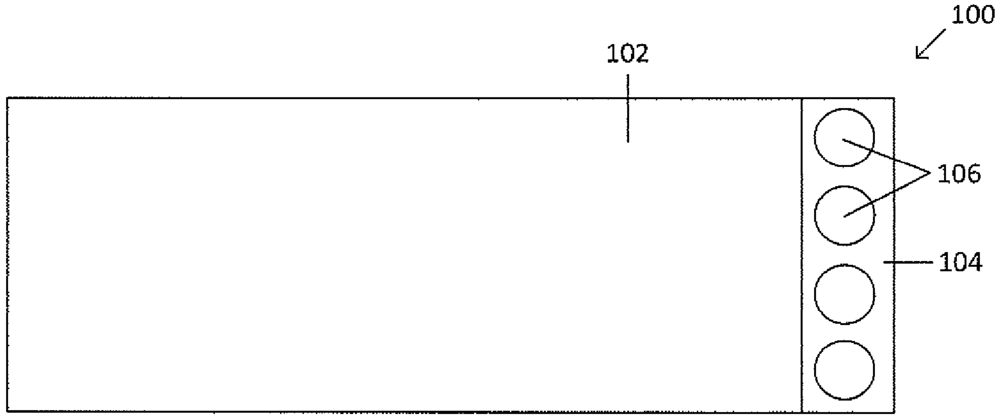

FIG. 1A shows an isometric view of a slide 100. FIG. 1B shows a top view of the slide 100. The slide 100 includes a main body 102 and a well section 104. The well section 104 includes wells 106. The main body 102 holds a suspension suspected of containing a target analyte; a fraction of a suspension, the fraction suspected of containing a target analyte; or, a target analyte having been previously extracted from a suspension. The wells 106 are configured to hold the target analyte. The slide 100 may be one or more pieces. The slide 100 is similar to a slide 110 except that the slide 100 is a singular piece, whereas the slide 110 is multiple pieces.

Figure 1C:
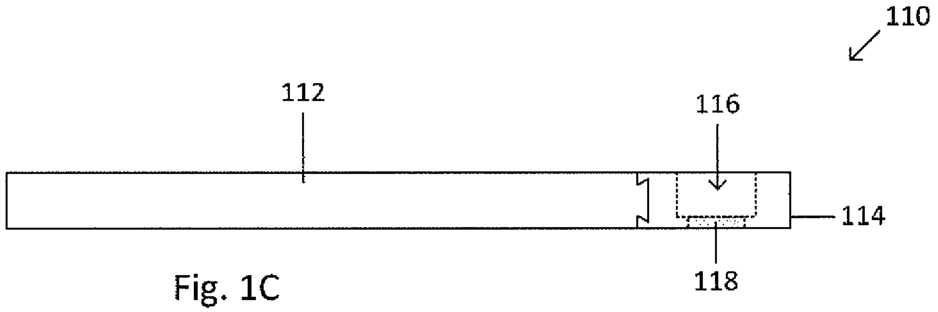
FIGS. 1C-1D show an example slide.
Figure 1D:
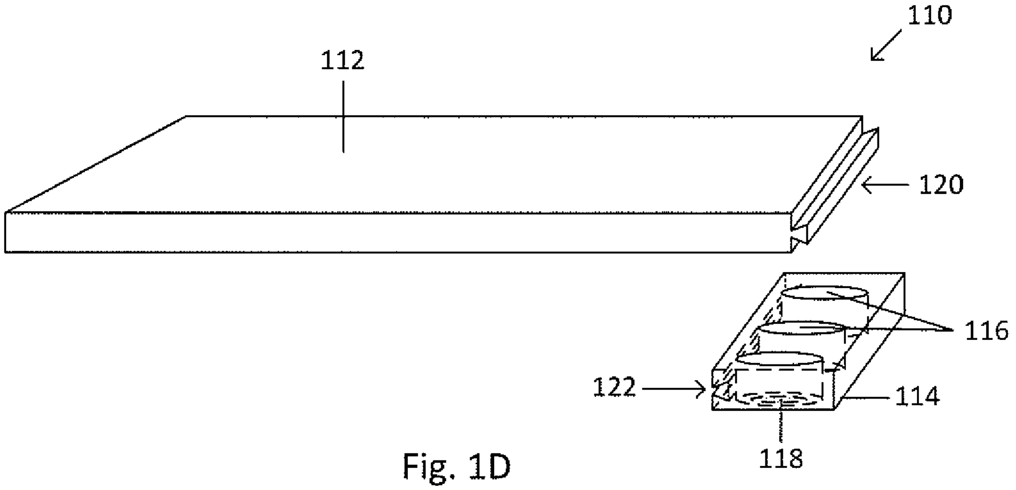

As seen in FIGS. 1C and 1D, a well section 114 may be removably attached to a main body 112. The main body 112 and the well section 114 may be removably attached by press fit or by an attachment system, such as clips, buttons, a tongue and groove, detents, or the like. The main body 112 may include a first attachment 120; the well section 114 may include a second attachment 122. The first and second attachments 120 and 122 are complementary. For example, the first attachment fits within the second attachment. When the well section 114 is removable, the well section 114 may be sized to fit into a second apparatus, such as a PCR thermocycler, for additional processing. Furthermore, wells 116 of the well section 114 may be joined together by attachment systems similar to the attachment system between the well section 114 and the main body 112. The wells 116 may each be separable from the well section 114 and the main body 112. The wells 116 may be removably attached by press fit or by the attachment system, such as clips, buttons, a tongue and groove, detents, or the like. When wells 116 are removable, the wells 116 may be sized to fit into a second apparatus, such as a PCR thermocycler, for additional processing.

The wells can be cylindrical, spherical, conical, frustoconical, or any appropriate shape. A bottom or sidewall of the wells can include a plug 118 so that a target analyte can be held within the wells after the target analyte has been drawn into the wells. The plug 118 may then be removed, thereby dropping the target analyte into another vessel (not shown) which may be used for further processing, such as a PCR tube for PCR thermocycling. Alternatively, the plug 118 may be punctured by a removal device (not shown), such as a needle, to remove the target analyte from the wells so that the target analyte can be inserted into another vessel (not shown) for further processing. When the target analyte has been conjugated with a particle capable of being attracted by a magnetic field, a bottom end of the well section 116 may also include a magnet (not shown) so that the target analyte is attracted to and held within the wells.

Figure 2A:
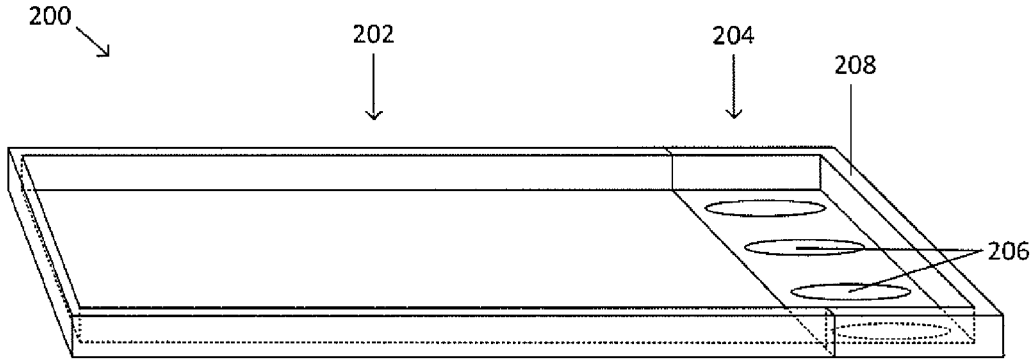
FIG. 2A shows an example slide.

FIG. 2A shows an example slide 200. The slide 200 is similar to slide 100 except that slide 200 includes a wall 208 to prevent a suspension, a fraction of a suspension, or a target analyte added to the slide 200 from spilling over the edge of the slide 200. The wall 208 surrounds the outer edges of a main body 202 and a well section 204. The well section 204 of the slide 200 includes wells 206. The well section 204 may be removably attached to the main body 202.

Figure 2B:
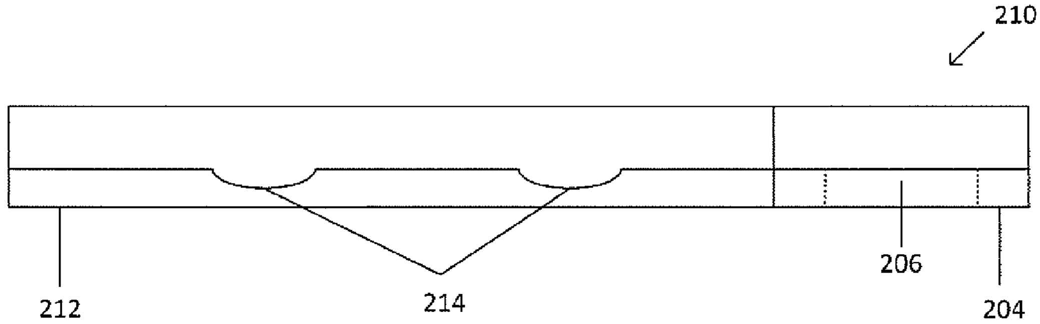
FIG. 2B shows an example slide.

FIG. 2B shows an example slide 210. The slide 210 is similar to the slide 200, except that the slide 210 includes a main body 212 with pools 214. The pools 214 may be filled with different solutions to wash, process, or label the target analyte. The target analyte may be dragged across the surface of the slide 210 and through the pools 214. For example, a first pool may include phosphate buffered saline to wash the target analyte; and, a second pool may include a solution with a fluorescent dye to label the target analyte. A processing pool may include a fixative, a detergent, or the like. The slide 210 may include one pool or may include many pools. The pools 214 may traverse the main body 212 or the pools 214 may partially extend across the main body 212.

Figure 2C:
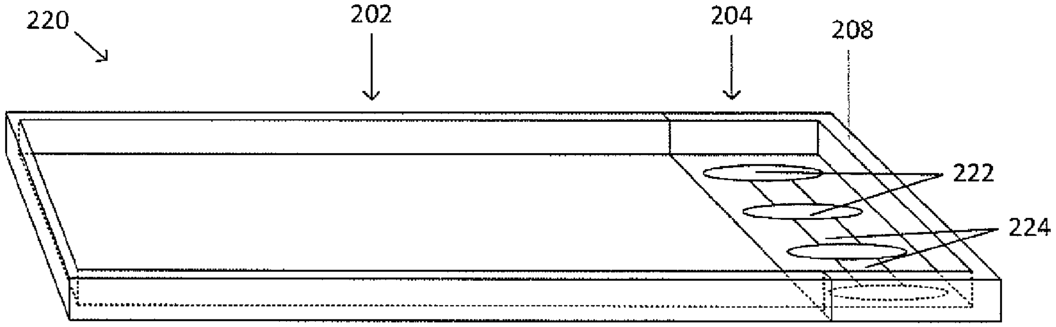
FIG. 2C shows an example slide.

FIG. 2C shows an example slide 220. The slide 220 is similar to the slide 200, except that the slide 220 includes wells 222 connected by channels 224. The wells 222 of the slide 220 are similar to the pools 214 of the slide 210 in that the wells 222 may be filled with different solutions to wash or label the target analyte. The target analyte may be dragged from well to well through the connecting channel 224. For example, a first well may include phosphate buffered saline to wash the target analyte; and, a second well may include a solution with a fluorescent dye to label the target analyte. One well, however, may be left empty to collect the target analyte.

Figure 3A:
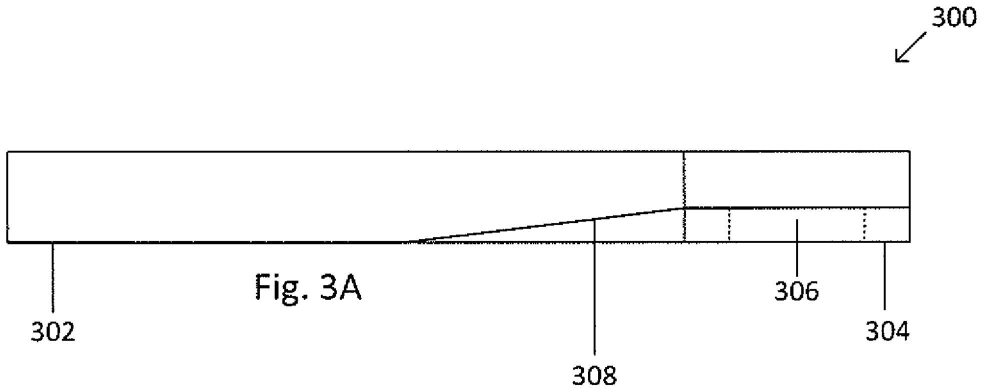
FIGS. 3A-3B show an example slide.
Figure 3B:
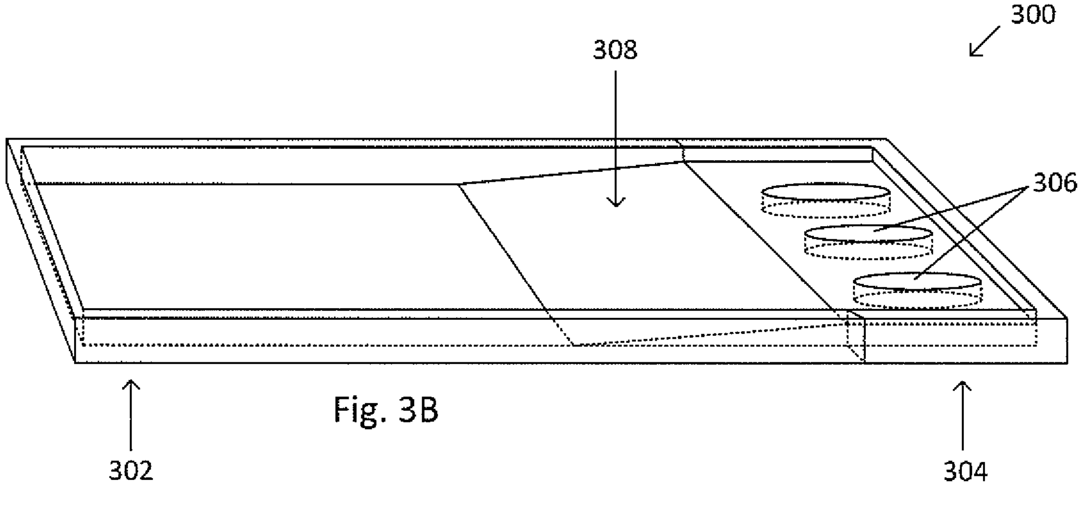

FIG. 3A shows a side view of slide 300. FIG. 3B shows an isometric view of the slide 300. The slide 300 is similar to the slide 200 except that slide 300 includes a ramp 308. The slide 300 includes a main body 302 and a well section 300. The main body 302 and the well section 304 are located on different planes. Separating the main body 302 and the well section 304 on different planes prevents a suspension, a fraction of a suspension, or a target analyte added to the slide 300 from contaminating or filling up wells 306, since the suspension, fraction, or target analyte may be moved actively (i.e. manually manipulated) instead of passively (i.e. gravity). The ramp 308 leads from the main body 302 to the well section 304. The main body 302 and the ramp 308 may be a singular piece, though the well section 304 may be removably attached to the ramp 308. The slide 300 may also include a wall.

Figure 4A:
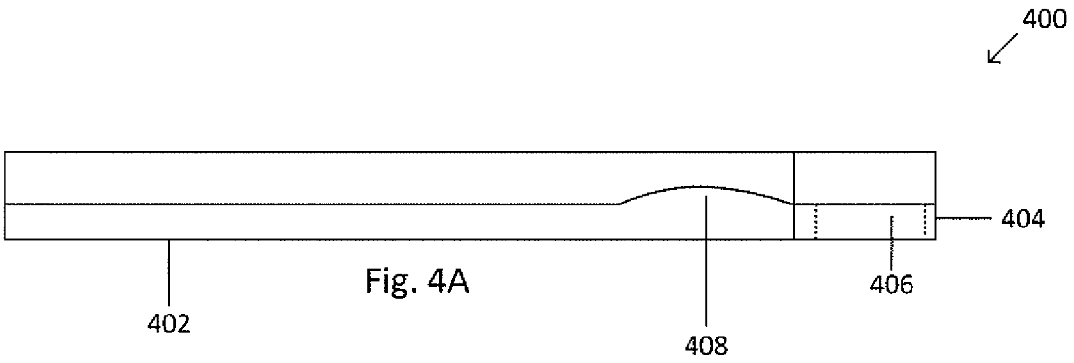
FIGS. 4A-4B show an example slide.
Figure 4B:
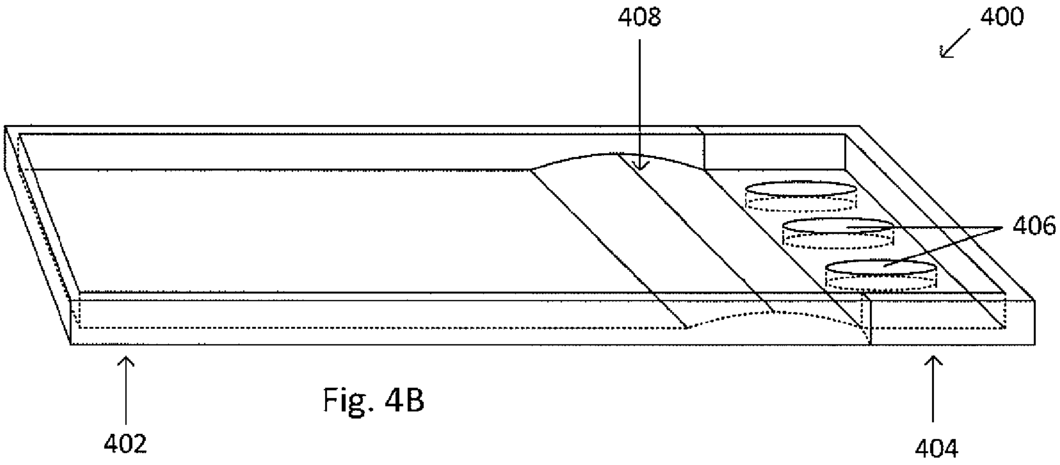

FIG. 4A shows a side view of slide 400. FIG. 4B shows an isometric view of the slide 400. The slide 400 is similar to the slide 200 except that slide 400 includes a separator 408. The slide 400 includes a main body 402 and a well section 400. The main body 402 and the well section 404 are located on the same plane. However, the main body 402 and the well section 404 are not in fluid communication, rather being separated by the separator 408. Separating the main body 402 and the well section 404 prevents a suspension, a fraction of a suspension, or a target analyte added to the slide 400 from contaminating or filling up wells 406, since the suspension, fraction, or target analyte may be moved actively (i.e. manually manipulated) instead of passively (i.e. gravity). The separator 408 prevents or breaks the fluid communication from the main body 402 to the well section 404. The main body 402 and the separator 408 may be a singular piece, though the well section 404 may be removably attached to the separator 408. The slide 400 may also include a wall.

Figure 5A:
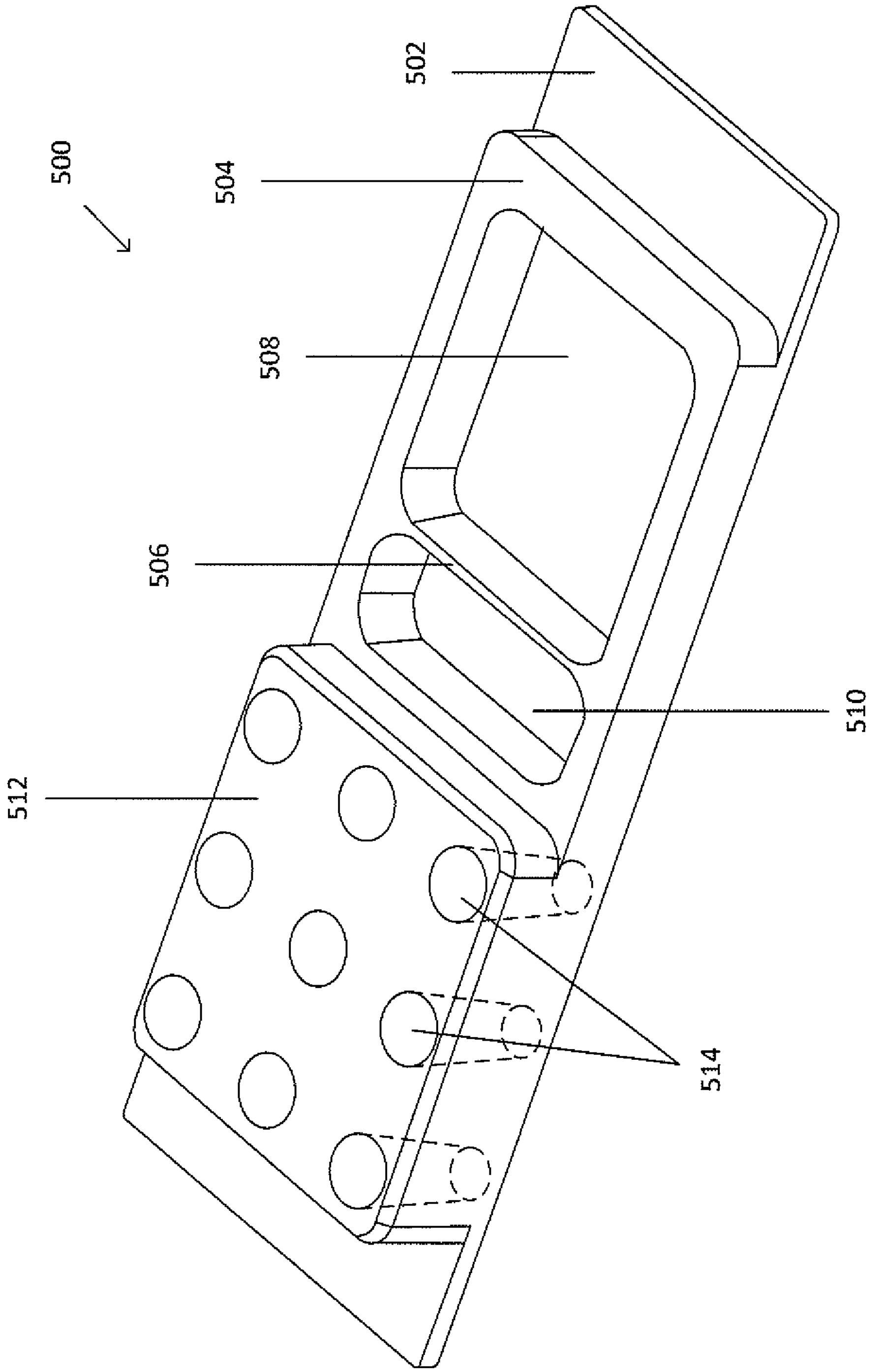
FIGS. 5A-5B show example slides.
Figure 5B:
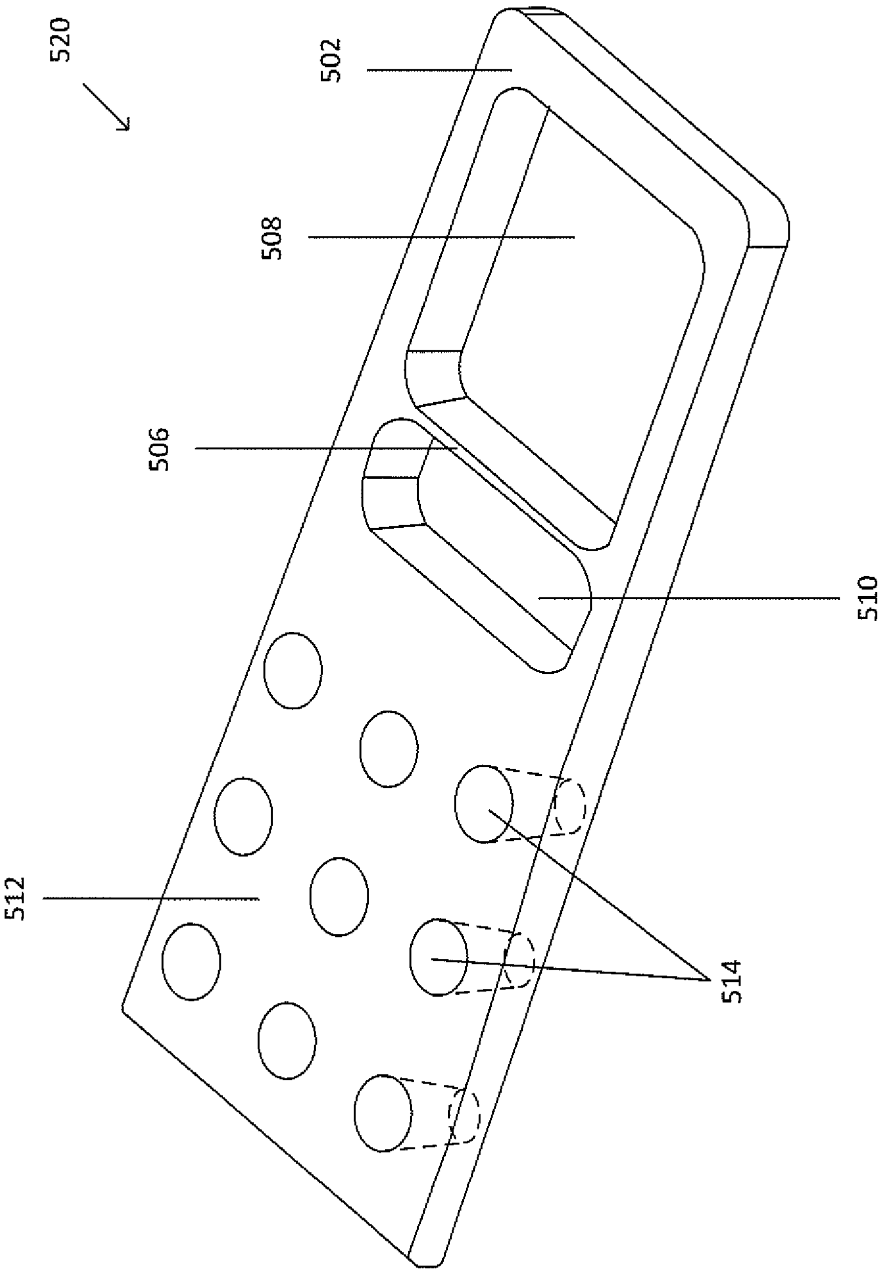

FIG. 5A shows a slide 500. The slide 500 includes a main body 502 and an enclosure 504 extending upwards from the main body 502, the enclosure 504 including four walls. A partition 506 extends from one side of the enclosure 504 to an opposite side to form two stations: a viewing station 508 and a holding station 510. The walls of the enclosure 504 and the partition 506 may be straight or tapered. The bottom edges and corners of the enclosure 504 and the partition 506 may be angular or rounded. The slide 500 also includes a well section 512 which includes wells 514. The well section 512 may extend upwards from the enclosure 504, may be co-planar with the enclosure 504, co-planar with the main body 502, or extend downward from the main body 502. The wells 514 may be straight or tapered and may hold a processing vessel (not shown), such as a PCR tube. At least one of the wells 514 may include a solution, such as phosphate buffered saline, water, mineral oil, DNA or RNA degraders (e.g. DNAZAP™) to wash or purge a cannula of the cell picker or the pipette. The bottoms of the wells may be closed, such as with an optically clear material, an opaque material, or a plug, or may be open. The viewing station 508, the holding station 510, and the wells 514 permit imaging through the bottoms of the respective segments to ensure the presence of the target analyte and to ensure successful transfer of the target analyte from one segment to another. Alternatively, a slide 520 is similar to the slide 500, except that the viewing station 508, the holding station 510, and the well section 512 may extend through the main body 502, thereby starting at a top side of the main body 502 and ending at a bottom side of the main body 502, as shown in FIG. 5B.

The viewing station 508, the holding station 510, and the well section 512 may have the same focal plane, such that imaging from one station or section to the next does require refocusing. Alternatively, the viewing station 508 and the holding station 510, may have the same focal plane as one another, and the well section 512 includes a known offset such that the focal plane of the well section 512 is adjusted from the focal plane of the the viewing station 508 and the holding station 510 by the known offset.

The viewing station 508 holds a sample to allow for imaging of a sample and picking of a target analyte from the sample. The holding station 510 holds already picked target analytes prior to being deposited into processing vessels. The holding station 510 may include a solution to wash, dye, or process the target analyte. The holding station 510 may be one segment or may be a plurality of segments which are sectioned off by more than one divider, such that n dividers across the holding station yields n+1 segments within the holding station, where n is greater than or equal to 1 (i.e. one wall across the holding station 510 forms two segments; two walls across the holding station 510 forms three segments; etc.). Each target analyte may then be transferred, such as by a cell picker or a pipette, to a processing vessel (not shown), such as a PCR tube, that sits within the wells 514 of the well section 512. After the target analyte has been transferred to the processing vessel (not shown), the processing vessel (not shown) may be removed to perform further analysis and/or processing on the target analyte. Alternatively, the target analyte may be transferred directly to the processing vessel (not shown) from the viewing station 508.

The slide may allow for the use of a variety of magnification objectives, such as up to 100×, including 10×, 40×, 60×, and 63×. The target analyte may undergo subsequent processing and/or analysis which include techniques for sequencing, such as nucleic acid sequencing, polymerase chain reactions ("PCR"), extracellular analysis and/or intracellular protein analysis such as intracellular protein staining, in situ hybridization ("ISH"), or branched DNA ("bDNA") analysis.

The slide or a portion thereof may permit for imaging, such that the slide is optically clear. Alternatively, the slide or a portion thereof may be opaque. The slide may be composed of glass, crystal, plastic, metal, or combinations thereof.

The slide may include a coating to reduce drag of the target analyte across the surface of the slide. Coatings may include, but are not limited to, pluronic, siliconizing reagent (e.g. SIGMACOTE®), or the like.

Figure 6:
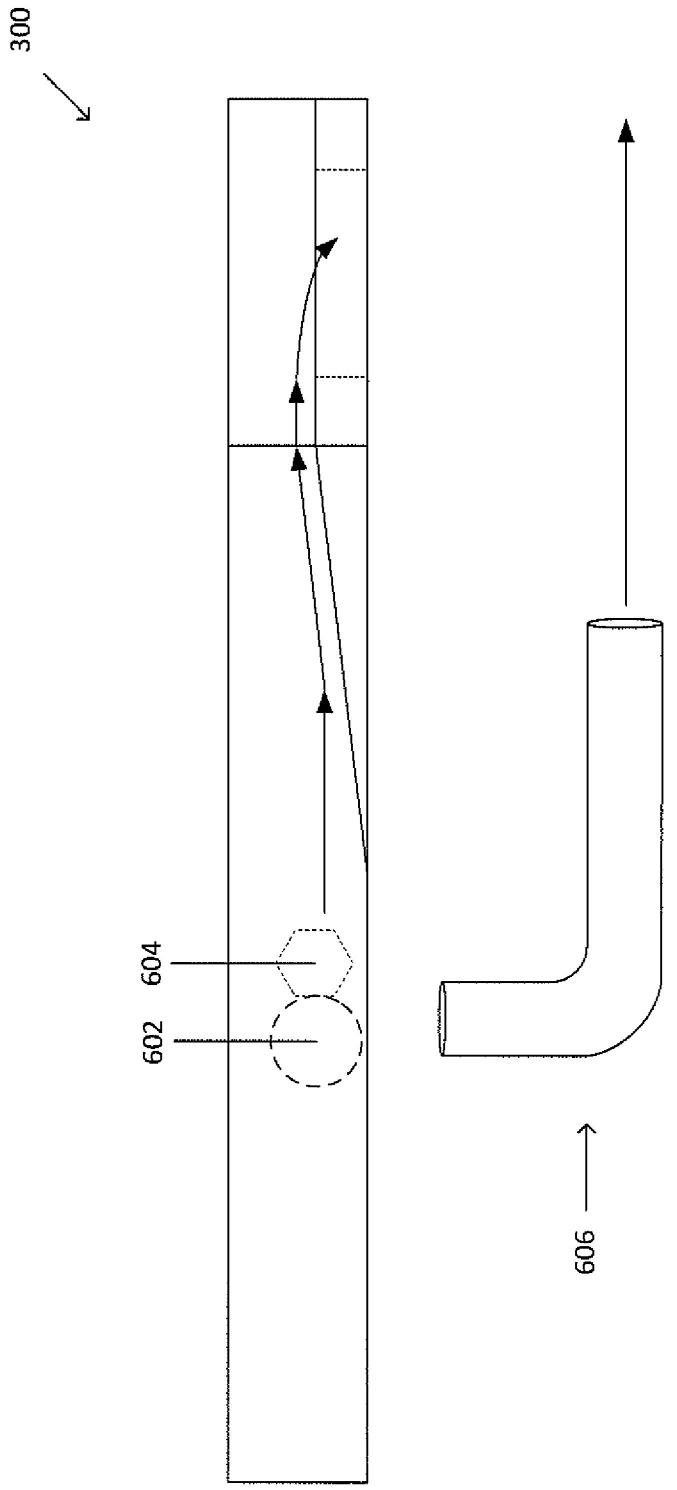
FIG. 6 shows a target analyte being manipulated on an example slide.

To collect the target analyte in a well, a suspension suspected of containing the target analyte or a fraction of a suspension suspected of containing the target analyte may be added to the main body section. The main body section may then be imaged to determine the presence and location of the target analyte. FIG. 6, for example, shows a target analyte 602 being manipulated on a slide 300. A probe 606 may be used to manipulate the target analyte 602, so as to move the target analyte 602 to the well. The probe 606 may manipulate the target analyte via magnetism—dragging the target analyte 602 across the main body or drawing the target analyte 602 into the probe 606, as the target analyte 602 was previously conjugated with a magnetic particle 604—or via suction—drawing the target analyte into the probe. The target analyte 602 may then be deposited into the well. When more than one target analyte is present, each target analyte may be deposited into individual wells or multiple target analytes may be deposited into an individual well. Alternatively, the target analyte may be picked, such as by a cell picker or a pipette, and then deposited within the well or associated processing vessel.

Once collected, the target analyte may be analyzed using any appropriate analysis method or technique, though more specifically intracellular analysis including intracellular or extracellular protein labeling; nucleic acid analysis, including, but not limited to, protein or nucleic acid microarrays; FISH; or bDNA analysis. These techniques require isolation, permeabilization, and fixation of the target analyte prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Slug, Ki-67, M30, MAGEA3, phosphorylated receptor kinases, modified histones, chromatin-associated proteins, and MAGE. To fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, Pap stain, Giemsa stain, or hematoxylin and eosin stain) may be used.

It should be understood that the method and system described and discussed herein may be used with any appropriate suspension or biological sample, such as blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target analyte can be a cell, such as ova or a circulating tumor cell ("CTC"), a circulating endothelial cell, a vesicle, a liposome, a protein, a nucleic acid, a biological molecule, a naturally occurring or artificially prepared microscopic unit having an enclosed membrane, parasites, microorganisms, viruses, or inflammatory cells.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

The invention claimed is:

1. A slide comprising:
a main body comprising
a viewing station to hold a sample for imaging of the sample and picking of a target analyte from the sample, and
a holding station to hold a picked target analyte prior to the picked target analyte being deposited into a processing vessel or the at least one well; and
a well section comprising at least one well,
wherein the well section is attached to the main body, and
wherein the holding station is located between the viewing station and the well section.

2. The slide of claim 1, wherein the main body and the well section are one piece.

3. The slide of claim 1, wherein the well section is removably attached to the main body.

4. The slide of claim 3, wherein the well section is sized to fit into a second apparatus for further processing or analysis.

5. The slide of claim 3, further comprising a plurality of wells, wherein at least one well of the plurality of wells is removably attached to the well section.

6. The slide of claim 1, further comprising a wall surrounding at least a portion of the main body.

7. The slide of claim 1, the at least one well further comprising a plug.

8. The slide of claim 1, the holding station comprising a solution to wash, process, or label the picked target analyte.

9. The slide of claim 1, further comprising at least one processing vessel located within at least one well.

10. The slide of claim 9, wherein the at least one processing vessel is a PCR tube.

11. The slide of claim 1, wherein a bottom of the viewing station, a bottom of the holding station, and a bottom of the least one well are optically clear for imaging.

12. The slide of claim 1, further comprising:
an enclosure extending upwardly from the main body, the enclosure comprising a first wall adjoined to a second wall and a fourth wall,
a third wall adjoined to the second wall and the fourth wall,
wherein the first and third walls opposite each other, and
wherein the second and fourth walls opposite each other; and
a partition extending from the first wall to the third wall,
wherein the viewing station includes the second wall, the partition, a first portion of the first wall and a first portion of the third wall, and
wherein the holding station includes the fourth wall, the partition, a second portion of the first wall and a second portion of the third wall.

13. The slide of claim 1, wherein the viewing station, the holding station, and the well section extend through the main body, thereby starting at a top side of the main body and ending at a bottom side of the main body.

14. The slide of claim 1, the holding station comprising at least one divider to form a plurality of segments within the holding station, wherein n dividers across the holding station yields n+1 segments within the holding station, and wherein n is greater than or equal to 1.

15. The slide of claim 1, wherein the viewing station, the holding station, and the well section have the same focal plane.

16. The slide of claim 1, wherein the viewing station and the holding station have the same focal plane as one another, and wherein the well section includes an offset such that the focal plane of the well section is adjusted from the focal plane of the viewing station and the holding station by the offset.

* * * * *